United States Patent [19]

Swisher et al.

[11] Patent Number: 4,898,593
[45] Date of Patent: Feb. 6, 1990

[54] AUTOTRANSFUSION BAG HOLDER

[75] Inventors: David R. Swisher, St. Louis; F. Thane DeWeese, Ladue, both of Mo.

[73] Assignee: Sherwood Medical Company, St. Louis, Mo.

[21] Appl. No.: 238,366

[22] Filed: Aug. 29, 1988

[51] Int. Cl.$^4$ ............................................... A61M 1/00
[52] U.S. Cl. .................................................... 604/319
[58] Field of Search .................... 604/317, 319–321, 604/4, 408, 410; 248/205.2, 250.2; 24/306, 442, DIG. 11, 448

[56] References Cited

U.S. PATENT DOCUMENTS

| | | | |
|---|---|---|---|
| 3,220,434 | 11/1965 | Garth | 137/374 |
| 3,363,627 | 1/1968 | Bidwell et al. | 128/276 |
| 3,559,647 | 2/1971 | Bidwell et al. | 128/276 |
| 3,847,152 | 11/1974 | Schachet | 128/276 |
| 3,861,390 | 1/1975 | Schachet | 128/276 |
| 3,924,624 | 12/1975 | Schachet | 128/276 |
| 4,105,031 | 8/1978 | Kurtz et al. | 128/276 |
| 4,439,190 | 3/1984 | Protzmann et al. | 604/319 |
| 4,704,106 | 11/1987 | Shave et al. | 604/319 |
| 4,781,707 | 11/1988 | Boehringer et al. | 604/319 |

FOREIGN PATENT DOCUMENTS

| | | | |
|---|---|---|---|
| 101042 | 2/1965 | Denmark | 248/205.2 |
| 1488315 | 7/1967 | France | 24/306 |

OTHER PUBLICATIONS

Pleur-evac® A-5005 Cat. Cut., DeKnatel Division, Pfizer Hospital Products Group, Inc., Floral Park, N.Y. 11001.

Primary Examiner—Jerome L. Kruter
Attorney, Agent, or Firm—Andrew J. Beck; Montgomery W. Smith; Richard D. Allison

[57] ABSTRACT

An attachment device for use in attaching a blood collection bag to the side of a chest drainage unit wherein the attachment device consists of an upper attachment arm removably fitting within an opening located on a removable bracket attached to the chest drainage unit and further including a pair of adhesive pads near the lower end of the side surface of the chest drainage unit and the collection bag holder.

9 Claims, 3 Drawing Sheets

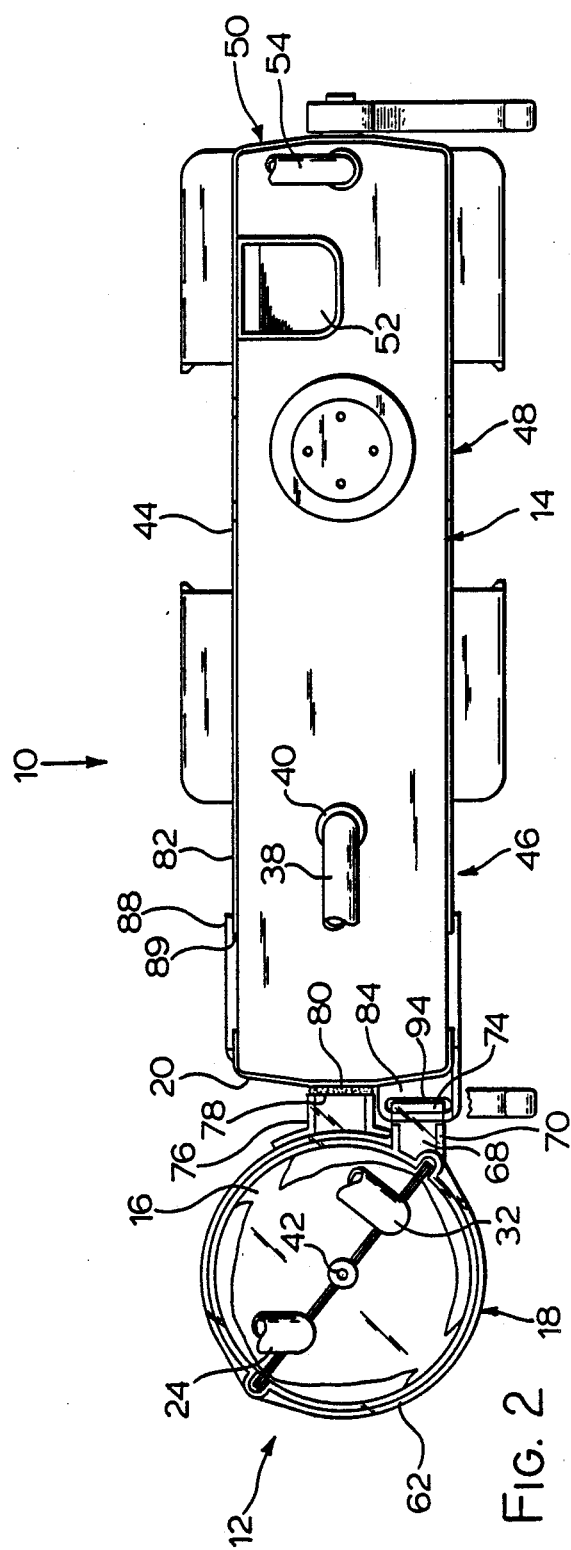
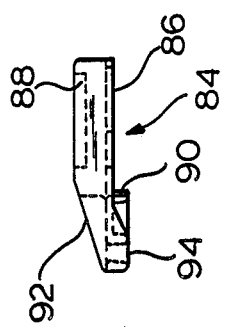
Fig. 2
Fig. 3

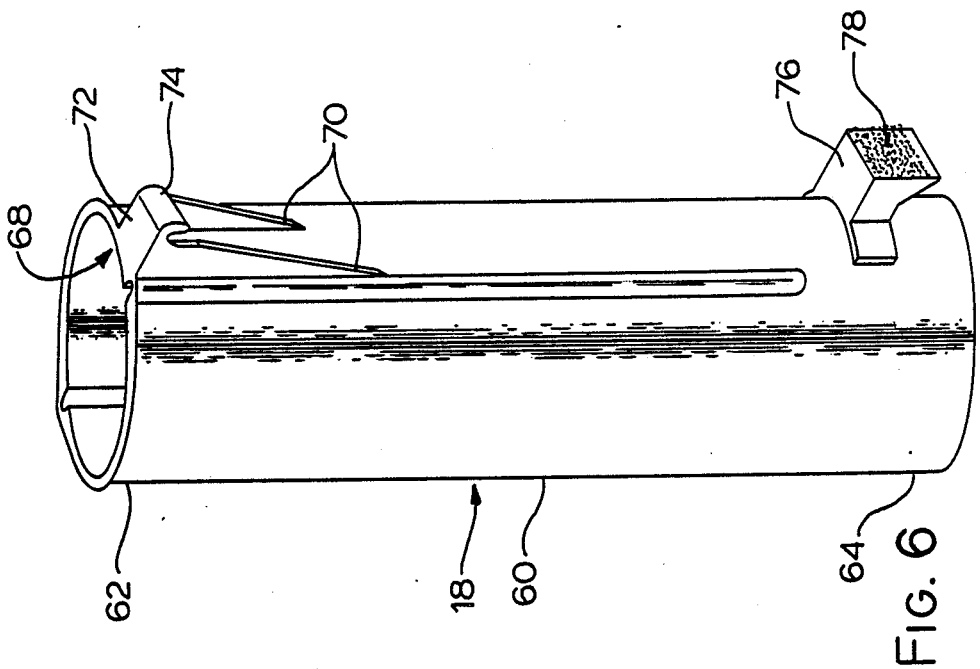
FIG. 6
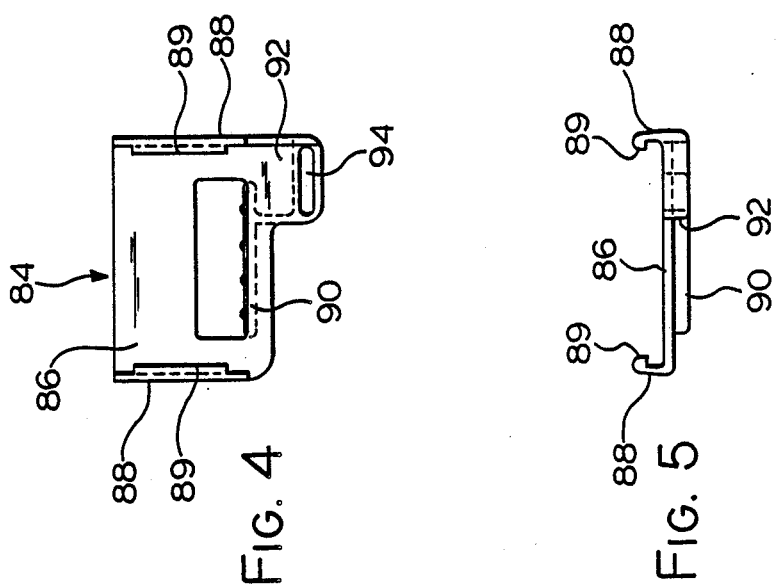
FIG. 4
FIG. 5

AUTOTRANSFUSION BAG HOLDER

TECHNICAL FIELD

This invention relates to an improved autotransfusion bag holder and more particularly to a device for attaching an autotransfusion bag to a chest drainage unit.

BACKGROUND

Recently, autotransfusion blood collection containers have been employed in combination with chest drainage units to store and reinfuse the fluid collected from a patient's pleural cavity. This reinfusion of the patient's own blood avoids the necessity of infusing stored blood from another person and thereby decreases the likelihood that a disease or infection will be transmitted to the patient.

A detailed discussion of autotransfusion is contained in Assignee's copending application, Ser. No. 014,508, entitled "Autotransfusion Device" filed on Feb. 13, 1987, which is incorporated herein by reference as if fully set forth below.

Generally, one form of autotransfusion utilizes a non-collapsible blood collection container which is connected to a chest drainage unit so that suction is applied through the collection container to the pleural cavity of a patient. The container collects the patient's blood as it is drained from the patient's pleural cavity. In order to reinfuse the blood into the patient from the non-collapsible container, the container must be vented to the atmosphere to allow the collected blood to flow from the container to the patient. Another form of autotransfusion utilizes a collapsible blood collection container. In this form of autotransfusion, a special apparatus must be used to maintain the bag in an expanded condition during blood collection due to the suction forces within the bag created by the chest drainage unit.

Presently, much of the research relating to autotransfusion is being directed to the development of the ideal blood collection container and therefore the development of a convenient method of attaching the blood collection bag to a chest drainage unit has largely been ignored. In most situations, the chest drainage unit with blood collection container must be set up and put into operation as quickly as possible in order to stabilize the patient and remove fluids from the chest cavity ouside the lungs to prevent the patient's lung from collapsing. During the rush to set up the chest drainage unit and blood collection container, it is not uncommon for the unit to be bumped or jostled while the various hoses are being attached to the patient and the source of suction. Prior attachment devices have consisted of pair of tongues and grooves which quite frequently become dislodged while the unit is being assembled or moved. This frequency results in the contamination of the blood collection container or at a minimum, a loss of valuable set up time and the further exposure of the patient's pleural cavity to the atmosphere or even a further buildup of fluid in the patient's pleural cavity.

OBJECTS AND SUMMARY OF THE INVENTION

It is therefore an object of the present invention to provide an improved attachment device for attaching a blood collection container to a chest drainage unit.

It is a further object of the invention to provide an attachment device which will withstand the bumping and jostling of the blood collection container and chest drainage unit during the assembly of the autotransfusion assembly.

Another object of the present invention is to provide an improved attachment device which will allow the blood collection container to be quickly and securely attached to the side of the chest drainage unit.

Still another object of the present invention is to provide an improved attachment device which will allow the blood collection container to be quickly removed from the side of the chest drainage unit when the container is suspended for the reinfusion of the blood back into the patient.

Presently, the state-of-the-art blood collection containers consist of a semi-rigid collection bag which is inserted into a rigid, generally cylindrical collection bag holder as disclosed in Ser. No. 014,508 referenced above. This collection bag holder supports the collection bag and helps to maintain the collection bag in its expanded shape as the fluids are suctioned from the patient's pleural cavity. In the present invention, an upper bracket is attached to the top of the chest drainage unit. An outwardly directed extension on the bracket extends from the side of the chest drainage unit. This extension engages a reinforced arm which projects outwardly from the top of the collection bag holder. The attachment device also includes a pair of adhesive pads for releasably engaging a horizontal projection positioned on the lower surface of the collection bag holder.

An advantage of the present invention is that the upper bracket on the chest drainage unit and the reinforced arm on the collection bag holder resist the horizontal movement of the collection bag and holder along the side of the chest drainage unit.

Another advantage of the present invention is that the adhesive pad on the side of the chest drainage unit engages the horizontal projection on the collection bag holder to prevent the vertical movement of the collection bag and collection bag holder along the side of the chest drainage unit.

Another advantage of the present invention is that once the reinforced arm is attached to the bracket, the projection on the lower end of the collection bag holder will automatically be aligned with the adhesive pad on the chest drainage unit.

BRIEF DESCRIPTION OF THE DRAWINGS

FIG. 2 is a top, partial cut-away view of a chest drainage system in accordance with the preferred embodiment of the present invention;

FIG. 3 is a side view of the upper bracket of the present invention;

FIG. 4 is a top view of the upper bracket of the present invention;

FIG. 5 is a front view of the upper bracket of the present invention; and

FIG. 6 is a perspective view of the collection bag holder of the present invention.

DESCRIPTION OF THE PREFERRED EMBODIMENT

Figure 1:
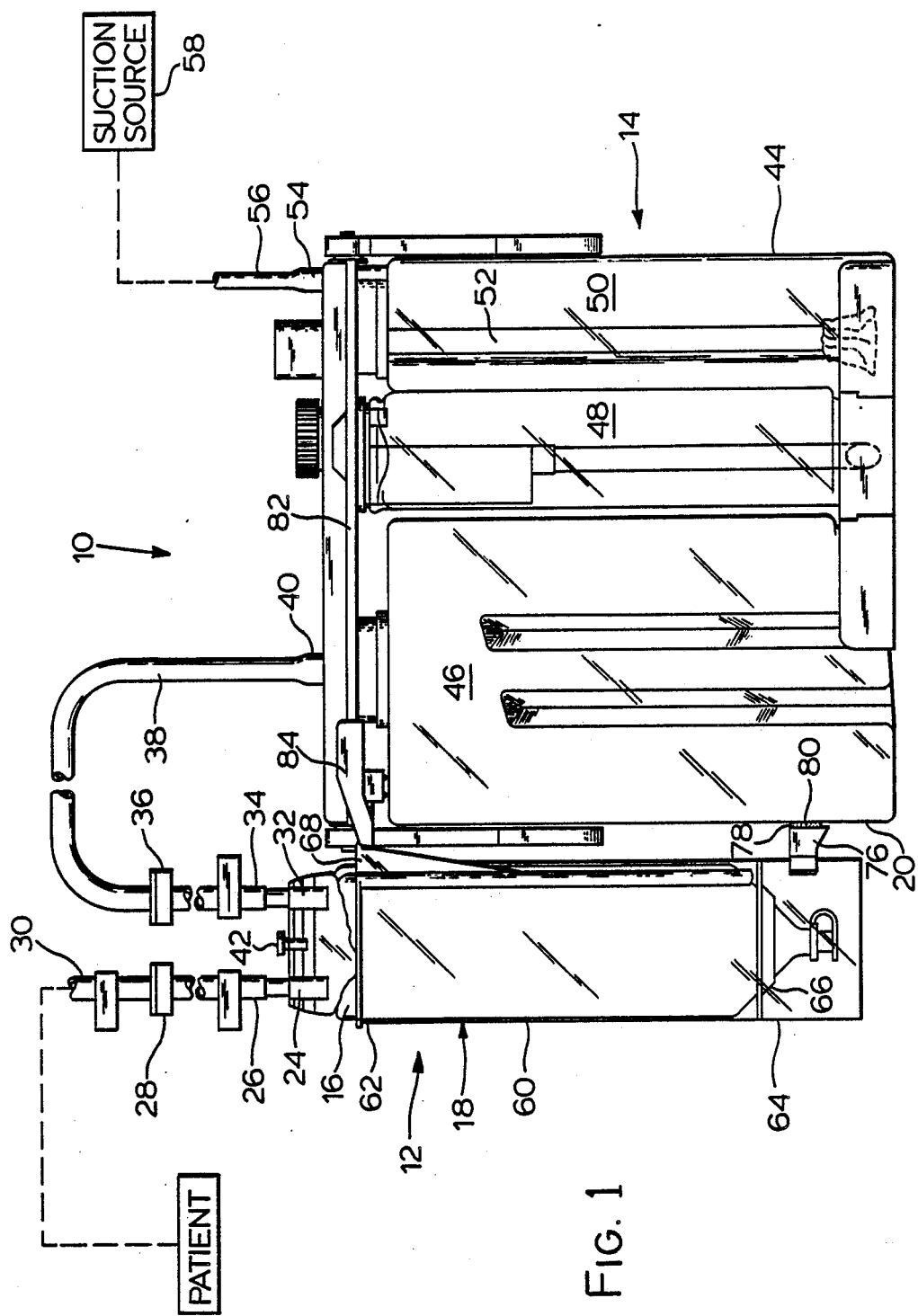
FIG. 1 is a side view of a chest drainage system including an autotransfusion device in accordance with the preferred embodiment of the present invention.

A chest drainage system 10 is shown including an autotransfusion blood collection device 12 connected to a chest drainage unit 14. The collection device 12 includes a blood collection bag 16 and a collection bag holder 18. The collection bag holder 18 supports the collection bag 16 in an expanded condition for receiving body fluids including blood from the pleural cavity of a patient. As will be discussed hereinafter, the collection bag holder 18 maintains the collection bag 16 in a generally fixed relation along the side 20 of the chest drainage unit 14.

In order to understand the importance of the present invention, it is necessary to understand the general operation of the chest drainage system 10. The blood collection device 12 includes an inlet 24 communicating with the interior of the collection bag 16 and shown connected to a tube 26. Tube 26 is connected through a tube connector 28 to the proximal end of a patient tube 30 which is connected through a catheter (not shown) to the pleural cavity of a patient. Spaced apart from the inlet 24 at the top of the collection bag 16 is a gas outlet 32 which communicates with the interior of the collection bag 16 and thereby inlet 24. The gas outlet 32 is connected to a tube 34 which, in turn, is connected to a suction tube 36 through a tube connector 38. Suction tube 36 is connected to an inlet 40 of the chest drainage unit 14. An auxiliary inlet 42 is located between the inlet 24 and the outlet 32. This auxiliary inlet 42 communicates with the interior of the collection bag 16 and is preferably a conventional self-sealing port which may be penetrated by a syringe needle for introducing a substance into the collection bag 16, for example, an anticoagulant.

The chest drainage unit 14 is shown generally for illustration purposes and includes a housing 44 which is preferably constructed of a rigid transparent plastic, such as a polycarbonate. The housing 44 includes a fluid collection chamber 46, an underwater seal chamber 48 and a manometer chamber 50. The manometer chamber 50 includes a vertical channel 52 which is open along its top end to the atmosphere. Additionally, a vacuum inlet 54 is attached along the top surface of the manometer chamber 50. The vacuum inlet 54 is connected by a flexible tube 56 to a conventional hospital suction source 58.

The collection bag holder 18 consists generally of a rigid elongate cylindrical body 60 having an open top end 62 and a substantially closed bottom end 64. The inner surface of the bottom end 64 includes a plurality of inwardly directed tapers 66 to support the collection bag 16 in the collection bag holder 18.

As illustrated in FIG. 6, the top end 62 of the collection bag holder 18 includes an upper arm 68 which extends outwardly from the body 60 of the collection bag holder 18 in a generally offset manner from the vertical center of the collection bag holder 18. The upper arm 68 includes a pair of reinforced ribs 70 which extend upwardly along the upper surface of the body 60 to reinforce the extension section 72 of the upper arm 68. The outer end of the extension 72 includes a downwardly directed hook section 74 which releasably engages the bracket 84.

The collection bag holder 18 also includes an outwardly directed projection 76, preferably spaced slightly above the bottom end 64 of the collection bag holder 18. The projection 76 extends outwardly from the body 60 of the collection bag holder 18 a distance approximately equal to the length of the upper arm 68 and the extension section 92 of the bracket 84 to align the collection bag holder 18 parallel to the side 20 of the chest drainage unit 14. The outer end of projection 76 is preferably flat and includes an adhesive pad 78 on its end surface. The adhesive pad 78 is preferably constructed of the hook and loop fastening material sold under the trademark VELCRO. A second adhesive pad 80 is located of the side 20 of the chest drainage unit 14 in alignment with the projection 76 and adhesive pad 78 of the collection bag holder 18.

The housing 44 of the chest drainage unit 14 includes a ridge 82 which extends around the entire top surface of the chest drainage unit 14. In the present invention, the bracket 84 releasably engages the ridge 82 of the chest drainage unit 14. The bracket 84 consists generally of a flat body surface 86, a pair of upwardly extending legs 88, and a spacing lip 90. The legs 88 extend upwardly from the side surface of the bracket body 86 and include a pair of inwardly directed lips 89 to releasably engage the ridge 82 of the chest drainage unit 14. The spacing lip 90 extends perpendicular to the legs 88 along the forward edge of the bracket body 86 to function as a means for orienting the bracket 84 in a predetermined position on the chest drainage unit 14. The bracket body 86 also includes an outwardly directed extension section 92 which, when the bracket 84 is attached to the chest drainage unit 14, extends horizontally from the side 20 of the chest drainage unit 14. The outer end of the extension section 92 includes an opening 94 which is designed to releasably engage the hook section 74 of the upper arm 68 to support the weight of the collection bag holder 18.

Once the bracket 84 is attached to the top surface of the chest drainage unit 14, the collection bag holder 18 is attached to the side 20 of the chest drainage unit 14 by inserting the hook section 74 into the opening 94. This automatically aligns the collection bag holder 18 with the side 20 of the chest drainage unit 14. Then, as the bottom end 64 of the collection bag holder 18 is released, the adhesive pad 78 on projection 76 will contact the adhesive pad 80 located of the side 20 of the chest drainage unit 14. Once these connections are made, the collection bag holder 18 is securely attached to the side 20 of the chest drainage unit 14 and the collection bag holder 18 is prevented from moving horizontally or vertically along the side 20 of the chest drainage unit 14.

What is claimed is:

1. An attachment device for attaching a collection bag to a drainage unit comprising
   a collection bag holder having top and bottom ends and including an upper arm near said top end and a lower projection spaced below said upper arm near said bottom end,
   a drainage unit having top and side surfaces and including an upper bracket with a vertically extending arm rigidly attached adjacent said top surface and a lower first fastener surface on said side surface,
   the upper arm further including an extension for releasably engaging an opening in said bracket of said drainage unit to form a first attachment means,
   said lower projection further including a second fastener surface for releasably engaging the first fastener surface on said side surface of said drainage unit to form a second attachment means, and
   wherein said first and second attachment means limit the horizontal and vertical movement of the collection bag holder about the drainage unit and wherein said second attachment means prevents rotation about the first attachment means.

2. The attached device of claim 1, wherein the bracket includes a plurality of upwardly extending legs for engaging said drainage unit and an extension section projecting outwardly from the side surface of said drainage unit wherein said extension section includes an opening therein for releasably engaging said downward extension of said upper arm.

3. The attachment device of claim 1, wherein the upper arm and lower projection extend outwardly from said collection bag holder in a generally horizontal manner and wherein the bracket and upper arm releasably support the weight of the collection bag holder.

4. The attachment device of claim 1, wherein the collection bag holder comprises an elongate and generally cylindrical container wherein the inner surface of said holder includes a means for supporting a collection bag therein.

5. The attachment device of claim 1, wherein said first fastener surface and said second fastener surface consist of a hook and loop material which fastens when pressed together arranged in a general mating relationship and the first fastener surface and the second fastener surface are aligned to contact each other when the extension of the upper arm engages said bracket.

6. A two part attachment device for attaching a collection bag to a drainage device comprising;
 a generally elongate collection bag holder having top and bottom ends and including an upper arm on said top end wherein said upper arm includes a downwardly projecting extension projecting therefrom,
 the collection bag holder further including an outwardly extending lower projection thereon spaced below said upper arm wherein said projection includes a first fastener means on its outwardly directed end surface,
 a drainage unit having a top surface and side surfaces and including an upper bracket with a vertically extending arm rigidly mounted thereon to releasably engage the downwardly projection extension of said upper arm to limit horizontal movement of the collection bag holder about the drainage unit, and
 said side surface including a second fastener means oriented generally in alignment with the first fastener means for releasable attachment of the collection bag holder to the side surface of the drainage unit to limit vertical movement of the collection bag holder about the drainage unit and wherein said first fastener means and said second fastener means prevent rotation of said upper bracket about said upper arm.

7. The attachment device of claim 6, wherein the bracket further includes a pair of upwardly extending legs for removably attaching to the top surface of the drainage unit and said bracket further including an elongate appendage extending outwardly from the side surface of the drainage unit and including a means for releasably receiving the downwardly extending projection of the upper arm.

8. The attachment device of claim 6, wherein the first fastener surface and the second fastener surface are comprised of a hook and loop material which fastens when pressed together oriented in a generally aligned mating relationship and wherein the first fastener surface projects outwardly in a generally horizontal manner from the collection bag holder to contact the second fastener means when the upper arm of the collection bag holder is inserted into the bracket of the drainage unit.

9. The attachment device of claim 6, wherein the lower projection extends outwardly from the bottom end of the collection bag holder further than the upper arm extends from the top end of the collection bag holder to align said collection bag holder generally parallel to the side surface of the drainage unit.

* * * * *